United States Patent [19]

Ash et al.

[11] 4,071,444
[45] Jan. 31, 1978

[54] PORTABLE CHEMICAL REACTOR FOR USE AS AN ARTIFICIAL KIDNEY

[75] Inventors: Stephen R. Ash, Lafayette; Philip G. Wilcox; David P. Kessler, both of West Lafayette, all of Ind.

[73] Assignee: Purdue Research Foundation, West Lafayette, Ind.

[21] Appl. No.: 731,826

[22] Filed: Oct. 12, 1976

[51] Int. Cl.² ............................................. B01D 31/00
[52] U.S. Cl. ............................... 210/22 A; 128/214 R; 210/232; 210/321 B
[58] Field of Search ............... 210/321 B, 22, 232; 128/214 R

[56] References Cited

U.S. PATENT DOCUMENTS

| 3,570,672 | 3/1971 | Bach | 210/321 B X |
| 3,682,817 | 8/1972 | Marx | 210/22 |
| 3,864,248 | 2/1975 | Granger et al. | 210/356 X |

FOREIGN PATENT DOCUMENTS 2,263,017  10/1975  France ..................... 210/321 B

*Primary Examiner*—Frank A. Spear, Jr.
*Attorney, Agent, or Firm*—John R. Nesbitt

[57] ABSTRACT

A small, portable, chemical reactor adapted to tap the venous blood supply of a patient, said device including a stack of semi-permeable membranes blood and dialysis materials in alternate chambers, said stack being held in sealed relationship by a single center bolt which facilitates quick assembly and disassembly.

11 Claims, 6 Drawing Figures

PORTABLE CHEMICAL REACTOR FOR USE AS AN ARTIFICIAL KIDNEY

BACKGROUND OF THE INVENTION

The artificial kidney was first successfully used on a patient in 1943. At that time, the machine consisted of a long tube of cellophane, a large tank of fluid called dialysate, and a very rapid blood flow from large tubes to arteries and veins. The blood flowed through the tubes of cellophane, and the dialysate around the cellophane. Impurities in the blood were removed by diffusion through the membranes, into the dialysate, a process termed "dialysis".

A typical modern version of a high flow rate dialyzer is shown by Bluemle, Jr. in U.S. Pat. No. 3,362,540. This patented construction is typical of the "cone type" dialyzers currently in use which are large (his unit is 30 inches in diameter) and typically require both semipermeable membranes to carry out the dialysis and separator discs both to protect the membranes against rupture and also, usually, to promote turbulent flow at the membrane surface so that the dialysate solution performs with maximum efficiency to remove impurities from the blood flowing on the other side of the membrane.

Such artificial kidney machines have many inherent disadvantages to the patient. They require the patient to be immobilized for long periods of time on the order of 6 hours, 3 times per week. Because of the speed at which contaminants and water are removed from the blood, patients often suffer a decrease in blood pressure causing weakness or nausea. Another person is required to operate the machine. Some patients require 12-24 hours to recover from the procedure. During the treatment a large volume of blood (on the order of 300-500 ml) must leave the body at one time. This "priming volume" requires the use of a great amount of saline solution to prime the device which tends to dilute the patient's blood considerably and also results in some blood loss at the end of the procedure. These machines require an arterial access to the bloodstream in order to obtain an adequately high flow rate on the order of 300 ml/minute. A high flow is necessary to mix the blood near membrane surfaces and even such high flow rate is considered to need augmentation to obtain better mixing, and hence more efficient impurity exchange at the membrane surfaces. A large dialysate reservoir on the order of 100-200L is required to accomodate the required dialysate flow of 1 to 5L per minute.

Various novel configurations appear in the art, such as that shown by Heden, U.S. Pat. No. 3,352,422, for the purpose of achieving maximum mixing at the membrane surfaces.

With existing devices, patients must have either tubes extending from arteries or veins, or a subcutaneous fistula into which needles are inserted. The blood flows through a long membrane tube or parallel plates or membrane which are contacted with a fast flow of dialysate fluid. The present artificial kidneys are bulky and require much auxiliary equipment for water purification and dispensing. The treatment is usually done in a specifically equipped room. Even if the treatment is performed in the patient's home the equipment, training and hospitalization costs are approximately $15,000.00 per year. The cost is inherently high because of the complexities and problems of the present artificial kidney machines.

SUMMARY OF THE INVENTION

The present device employs venous blood access which is easier (veins are closer to the body surface and more numerous) and safer than using an arterial blood supply. The venous blood is also under much less pressure than arterial blood and the present device employs a low pressure system which is a desirable object because the danger of membrane rupture is considerably reduced over high volume, high pressure systems.

The present device uses a much slower blood treatment rate than conventional dialysis machines, on the order of 60 vs. 300 ml/minute. This is an advantage because it involves slower fluid shifts to the patient, more efficient dialysis, and lower energy requirements.

The unit is small and lightweight. It will not necessarily immobilize the patient, but is fully portable. No auxiliary equipment is needed since this device is completely self-contained. The unit is activated by the patient, or by a lightweight motor. Direct contact is maintained between the membranes and a slurry of sorbents. The sorbents allow dialysis without large volumes of water.

Efficient dialysis can be obtained since very close membrane spacing is used and a thin blood column is maintained without the usual disc separators. The direct contact of slurry with membranes allows maximum gradient across the membrane. The parallel membranes are designed to be "self-cleaning", that is, blood is totally removed when the membranes are empty. Thus, stagnant areas of blood or dialysate are eliminated and the "priming volume" is nearly zero. The efficiency approaches that of present dialysis units, which use rapid blood and dialysate velocity to reduce stagnant areas, and yet cost of the present device is substantially less than the conventional system.

The unit will operate dialy for a period of 4-5 hours. It removes the blood contaminants slowly; thus, the patient feels less discomfort because of minimal disruption of the balance of solutes in his body fluid. Daily operation is quite tolerable to the patient because he is not immobilized during dialysis and has less decrease in blood pressure.

No direct blood pump is required for this system as the blood is drawn into the unit and forced out by varying the pressure within the dialysate chamber. The blood pump normally requires considerable energy and causes some change to blood components.

THE DRAWINGS

DETAILED DESCRIPTION OF THE INVENTION

Figure 1:
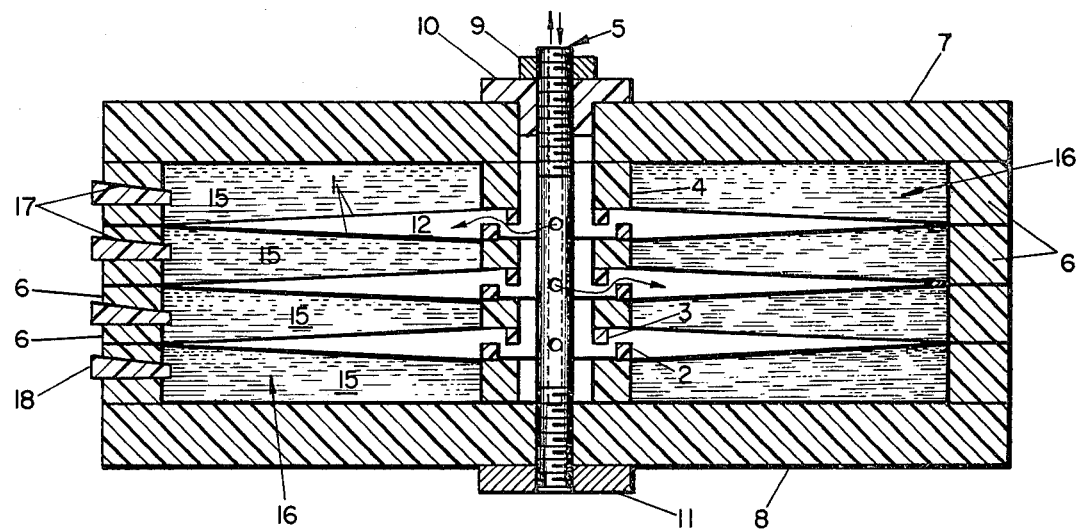
FIG. 1 is a cross-sectional view of the present device.
Figure 2:
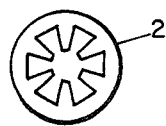
FIG. 2 is a top plan view of a gasket used in the subject device.
Figure 3:
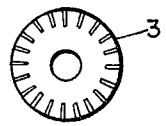
FIG. 3 is a top plan view of another gasket used in the subject device.
Figure 1A:
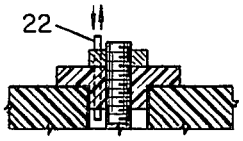
FIG. 1A is a partial cross sectional view of the device shown in FIG. 1, particularly illustrates an alternate blood flow construction.
Figure 4:
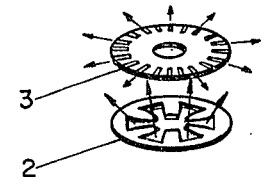
FIG. 4 is a diagrammatic representation of the blood flow path through the gaskets shown in FIG. 2 and 3.
Figure 5:
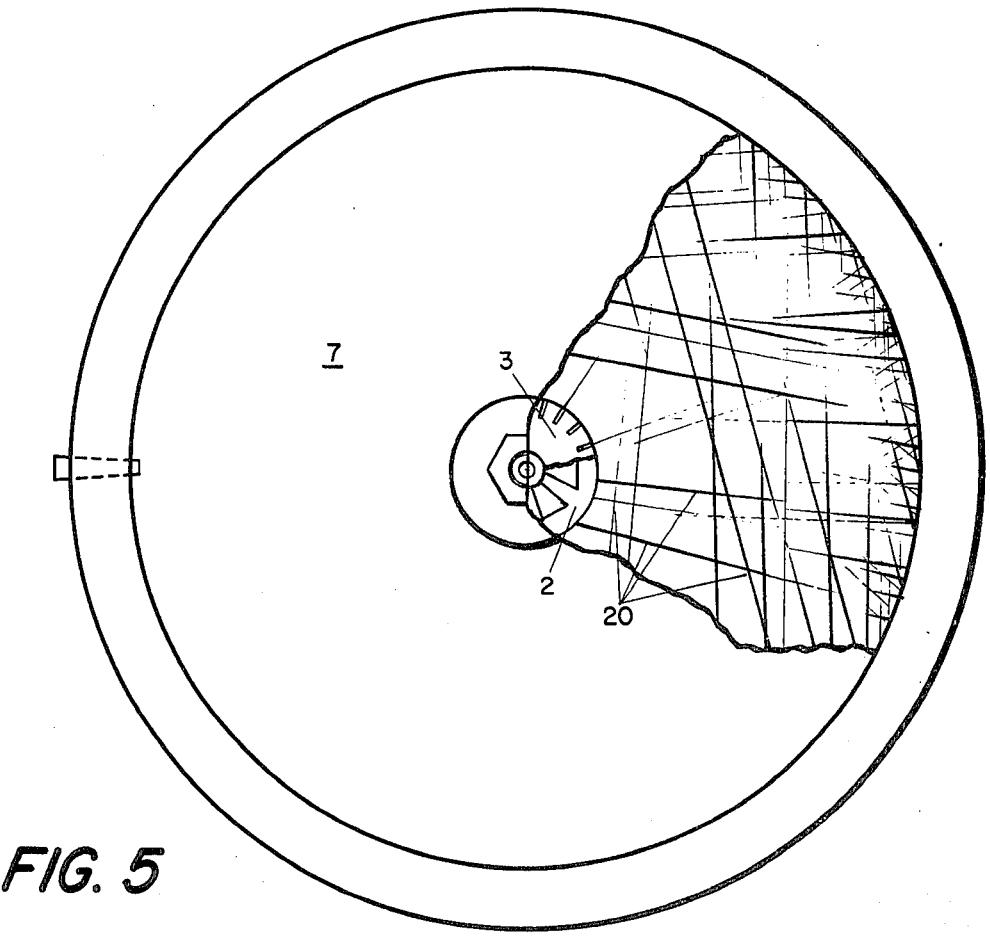
FIG. 5 is a top view of the device with a portion broken away to show blood flow distribution within the device.

The present dialyzer device comprises a stack of resilient semi-permeable membranes 1 separated by central distribution gaskets 2 and 3, and further including spacers 4 which permit blood to be introduced through central core bolt 5. An alternate arrangement may be used whereby a separate blood supply to 22 is used, as shown in FIG. 1A. Gaskets 2 and 3, and even spacer 4 may be of unitized construction. The stack of membranes, gaskets and spacers are all clamped into sealing relationship by outer rings 6 and top end plate 7 and bottom end plate 8 when nut 9 is tightened against end plug 10 thereby compressing the entire stack between plug 10 and bolt 5.

When the stack of semi-permeable membranes are thus assembled, a first chamber 12 is provided into which blood may flow from central bolt 5 through gasket 2 and then through gasket 3, and a second chamber 15 is provided into which dialysis material 16 may be introduced and withdrawn through ports 17. Plugs 18 may be used to seal a given dialysis material inside chamber 15 for the entire dialysis operation or, if desired, a low pressure pump (such as a diaphram pump operated by the patient's own breathing) may be connected to the dialysate chambers to create an oscillation inside the dialysate chamber 15 which expedites dialysis.

The dialysate chambers 15 are filled with a solution 16 containing water, activated charcoal, zirconium phosphate, zirconium oxide and urease or other sorbents. These components absorb the urea and creatinine drawn through membranes 1 very readily and, due to the thinness of the blood layer between adjacent membranes, very efficient dialysis is achieved. Of course, this thin layer concept may also be used to achieve "self cleaning" on the dialysate side, when the dialysate side is connected to an external dialysate supply. Even the absence of sorbents, this self cleaning action will increase the efficiency of dialysis.

Because gaskets 2 and 3 are central and do not extend to any substantial distance away from the core bolt 5, when pressure is exerted inside the dialysate chamber 15, there are no impediments between the semi-permeable membranes 1 to prevent substantially complete expulsion of the blood therebetween. All known prior art devices have discs interposed between the membranes, for one reason or another, and hence an impediment to complete expulsion of blood from the device is created. As a result, not all the blood operated upon is returned to the body in these prior art devices, and substantial cleanup operations are required before these devices may be reused. In the present device, assembly and disassembly is accomplished by stacking the components and tightening a single nut 9 on bolt 5. This seals the permeable membranes against the blood flow regulator gaskets 2 and 3 and also seals the membranes between outer rings 6. Another novel and useful feature of the present invention is that when membranes 1 are made of cellophane, the membranes inherently contain striations or passages 20 therein. These passages cause blood to infiltrate the entire chamber 12 between membranes 1 in a rapid and fairly uniform manner. This infiltration action is further expedited when the "grain" of alternate membranes are placed at right angles to one another. This rapid injection of blood into the treatment chamber is accomplished at very low pressures such as are encountered in the venous system.

When a dialysis cycle is completed (usually about once a minute with a typical device having an outer diameter of 5 inches) the dialysate chamber 15 is pressurized from an external source, and the blood flow is reversed in center bolt 5 and returned back to the body.

Due to the small volume of blood inside the dialyzer at one time, it is possible to detoxify certain drug overdose blood conditions without radically changing the normal blood constituents of a significant portion of a patient's blood supply. Due to the relatively smaller capacity of the present device, compared with high speed arterial blood supplied dialysis devices, certain drugs may be administered into the blood locally without any significant effect on a patient's entire blood supply and certain radical therapy may be applied to a relatively small percentage of a patient's blood over a given period of time without any serious impact on his blood supply as a whole.

We claim:
1. A dialysis device, comprising a sealed outer casing which is divided internally by at least one flexible membrane into at least one chamber adapted to receive blood, and at least one other chamber adapted to receive dialysis material,
   a blood flow passage directly connected to said one chamber to provide blood flow in one direction into said one chamber through said blood passage and to provide blood flow in the opposite direction away from said one chamber through said blood passage,
   pressure control means connected to said other chamber,
   whereby decreasing the pressure in said other chamber causes blood to be drawn into said one chamber through said blood passage, and increasing the pressure in said other chamber causes blood to be forced out of said one chamber through said blood passage.
2. The device of claim 1 in which said blood flow passage is connectable with a single venous blood access to a patient, and wherein said pressure control means exerts low pressure sufficient to provide slow blood treatment of a patient connected with said device through said single venous blood access.
3. A dialysis device comprising:
   a top plate and a bottom plate having central apertures therein;
   at least one peripheral spacer having a solid peripheral portion and a hollow central portion;
   at least two semi-permeable flexible membranes having central apertures therein;
   central gasket and spacer means having a bore therein;
   a bolt having compression means thereon to clamp said top and bottom plate therebetween, said bolt being sized to fit in the bore of said central gasket and spacer means;
   said flexible membranes being captured in sealing relationship at their outer peripheries between said top and bottom plates with said peripheral spacer therebetween, and being captured in sealing relationship at their central aperture with said central gasket and spacer means therebetween upon insertion of said bolt in the central aperture of said plates, gasket and spacer means and membranes and the tightening of said compression means on said bolt, such that the gasket and spacer means, and the top and bottom plates, and peripheral spacer are all placed in compression by said compression means on said bolt with a sealed chamber being thereby formed for receiving fluid in direct contact with said membrane; and passage means for providing a single fluid path both to and away from said chamber and through which fluid is conducted into said chamber and from which fluid is conducted away from said chamber.

4. The device according to claim 3 in which said membranes have a plurality of striations therein.

5. A method of operating a dialysis apparatus having adjacent resilient semi-permeable membranes forming at least two chambers within a casing, one of said chambers being charged with blood inflow and providing blood outflow through a single passage and another adjacent chamber being charged with dialysate material, which method comprises: alternately lowering and increasing the pressure in said dialysate chamber thereby first expanding the blood chamber to draw in a small amount of blood for dialysis through said single passage, and then expelling the dialyzed blood from the blood chamber through said single passage whereby slow blood treatment is steadily achieved.

6. The process according to claim 5 in which the blood in introduced into and expelled from said chamber through a centrally located passage.

7. A chemical reactor device for hemodialysis in which at least two semi-permeable elastic membranes are disposed between annular rings at the outer periphery of the membranes, at least one central spacer disc having a diameter substantially less than said annular rings, with said spacer disc including passage means to permit blood flow therethrough to and from a first chamber between said membranes, said device also including a single passage for conducting blood to and from said first chamber through said spacer disc, and said device also including a top disc and a bottom disc which, together with said membranes, define a second chamber, said second chamber having passage means communicating therewith to the exterior of said device whereby the contents of said second chamber, and hence pressure therein, may be controlled from the device exterior independently of said passage means in the central spacer disc.

8. The device according to claim 7 in which the device includes a central bore extending through said top and bottom discs, said membranes and said spacer disc including blood passage means, said bore being sized to receive a bolt in said bore with said bolt having said single passage therein to provide for said interior blood passage, said bolt also having at least one port therein between said single passage and its outer surface, said bolt port being in communication with the blood passage means of said spacer disc whereby blood may be admitted from the exterior of the device into the said first chamber of the device through said single passage and withdrawn from said chamber and conducted to the exterior of said device through said single passage.

9. The device according to claim 8 in which said bolt has a head of larger diameter than the said central bore of the device at one end, and said bolt being adapted at its other end to receive a compression type fastener, a compression fastener on the end of said bolt adapted to receive it whereby, upon tightening said fastener, compression forces are exerted both on said spacer disc, top and bottom plates and annular rings such that the said membranes are captured therebetween and sealed.

10. A chemical reactor device for hemodialysis in which at least two semi-permeable elastic membranes are disposed between a peripheral spacer at the outer periphery of the membranes and at least one central spacer, said central spacer having passage means to permit blood flow therethrough to and from a first chamber between said membranes, and said membranes having striations therein with said membranes being closely positioned with respect to one another and being oriented so that said striations facilitate blood flow from said central spacer toward the outer periphery of the chamber, said device also including means which, together with said membranes, define a second chamber receiving dialysate material in contact with said membranes at the side thereof opposite to that in contact with said blood spread through said first chamber.

11. The device according to claim 10 in which the membrane striations are arranged at right angles to one another between adjacent membranes whereby uniform blood flow is permitted.

* * * * *